United States Patent [19]

Saito et al.

[11] Patent Number: 4,849,136
[45] Date of Patent: Jul. 18, 1989

[54] PROCESS FOR PRODUCING 7-AMINO-6-DEMETHYL-6-DEOXYTETRACYCLINE

[75] Inventors: Yutaka Saito, Machida; Masaji Kasai, Fujisawa, both of Japan

[73] Assignee: Kyowa Hakko Kogyo Co., Ltd., Tokyo, Japan

[21] Appl. No.: 201,872

[22] Filed: Jun. 3, 1988

[30] Foreign Application Priority Data

Jun. 11, 1987 [JP] Japan .............................. 62-146056
Jul. 21, 1987 [JP] Japan .............................. 62-181640

[51] Int. Cl.⁴ .................................................. C07C 49/423
[52] U.S. Cl. ................................. 260/351.5; 260/351.3
[58] Field of Search ............... 260/351.5, 351.1, 351.3, 260/377, 383, 372

[56] References Cited

U.S. PATENT DOCUMENTS 3,043,875 7/1962 Beereboom et al. .
3,226,436 12/1965 Petisi et al. .
3,239,499 3/1966 Rennhard et al. .
3,341,585 9/1967 Bitha et al. .................... 260/559
3,403,179 9/1968 Zambrano .
3,901,942 8/1975 Bernardi et al. .

FOREIGN PATENT DOCUMENTS 696488 10/1967 Belgium .
M311 3/1970 France .................... 260/351.5

OTHER PUBLICATIONS

J. Org. Chem., 36, 723 (1971).
J. Med. Chem., 10, 44 (1967).
J. Med. Pharm. Chem., 5, 538 (1962).
Farmaco. Ed. Sci., 30, 736 (1975).

Primary Examiner—Glennon H. Hollrah
Assistant Examiner—Raymond Covington
Attorney, Agent, or Firm—Fitzpatrick, Cella, Harper & Scinto

[57] ABSTRACT

This invention provides a new process for producing 7-amino-6-demethyl-6-deoxytetracycline (Compound 3) which is an intermediate for the synthesis of minocycline.

Compound 3 can be obtained by reduction of Compound 1 using a dithionite as reducing agent.

This invention also provides a method to produce Compound 3 from Compound 2 in one pot.

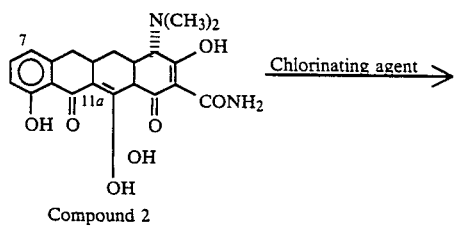

Compound 2

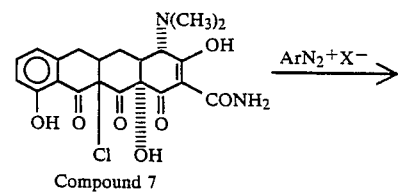

Compound 7

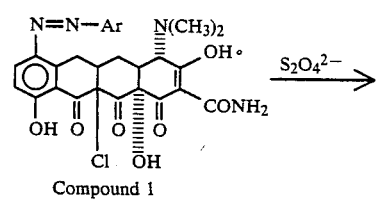

Compound 1

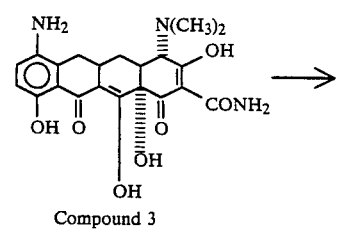

Compound 3

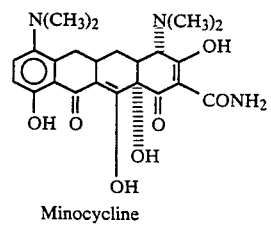

Minocycline (wherein Ar denotes a substituted aryl group, and X stands for the residue of a mineral acid from which hydrogen atom has been eliminated).

7 Claims, No Drawings

PROCESS FOR PRODUCING 7-AMINO-6-DEMETHYL-6-DEOXYTETRACYCLINE

BACKGROUND OF THE INVENTION

This invention relates to a process for producing 7-amino-6-demethyl-6-deoxytetracycline which is an intermediate for the synthesis of minocycline—an antibiotic having a broad antibacterial spectrum.

The following methods have been known for the synthesis of minocycline using 6-demethyl-6-deoxytetracycline (hereinafter referred to as Compound 2) as starting material.

Method 1

Compound 2 is nitrated to give an isomeric mixture of 7-nitro compound and 9-nitro compound, from which 7-nitro isomer is isolated. Minocycline can be obtained by subjecting the 7-nitro compound to catalytic reduction to give 7-amino-6-demethyl-6-deoxytetracycline (Compound 3), followed by reductive dimethylation [J. Org. Chem., 36, 723 (1971); J. Med. Chem., 10, 44 (1967); and J. Med. Pharm. Chem., 5, 538 (1962)].

Method 2

The 9-position of Compound 2 is protected with a tert-butyl group and a nitro group is introduced at the 7-position. The nitro group is converted to an amino group by catalytic reduction, followed by reductive dimethylation and removal of the protective group, to obtain minocycline [Farmaco. Ed. Sci., 30, 736 (1975); and Japanese Published Examined Patent Application No. 41458/1982, U.S. Pat. No. 3,901,942].

Method 3

Compound 2 is allowed to react with an azodicarboxylic acid diester, and the product thus obtained is subjected to acid hydrolysis or hydrogenolysis to form Compound 3, followed by reductive dimethylation, to obtain minocycline (Japanese Published Examined Patent Application Nos. 37666/1975 and 15594/1977, U.S. Pat. No. 3,403,179).

Method 4

Compound 2, with its 11a-position protected by halogenation or with the carbonyl at 11-position protected as enamine, is subjected to diazo coupling reaction. The resulting azo compound is treated with hydrogen in the presence of a noble metal catalyst to effect dehalogenation and hydrogenolysis of the azo group to form, Compound 3, followed by reductive dimethylation, to give minocycline (Belgian Pat. No. 696488, and U.S. Pat. No. 3,239,499).

Of the four methods enumerated above, Methods 1, 3 and 4 employ compound 3 as the intermediate for the synthesis of minocycline. In Method 1, an isomeric mixture is formed in the step of introducing the nitrogen-containing functional group, and formation of 9-substituted isomer in addition to intended 7-substituted compound complicates the purification operations and lowers the yield of the final product, minocycline. This problem is surmounted in Method 2, but the product yield is also low because of the supplementary reaction steps involved, such as the steps for the protection and deprotection.

Method 3 has the problem that, in the addition reaction of the azodicarboxylic acid diester, an expensive reagent must be used and a corrosion-resistant reactor need be employed because of the corrosive solvent (e.g., methanesulfonic acid) to be employed.

Detailed below is Method 4 which is closely related to the process of this invention.

U.S. Pat. No. 3,239,499 discloses a process, which comprises (1) allowing Compound 2 to react with a halogenating agent to form a 6-demethyl-6-deoxy-11a-halotetracycline represented by the following general formula (IV),

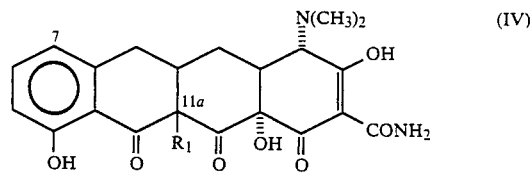

(wherein $R_1$ denotes chlorine or fluorine atom); (2) subjecting compound (IV) to diazo coupling reaction with a diazonium compound represented by the following general formula (V),

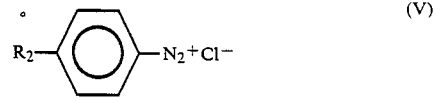

(wherein $R_2$ stands for chlorine atom or sulfonic acid group) to form a 6-demethyl-6-deoxy-11a-halo-7-substituted-arylazotetracycline represented by the following general formula (VI) (hereinafter referred to as Compound 6),

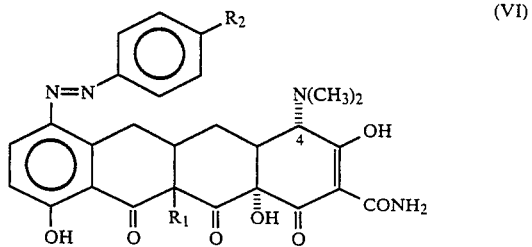

(wherein $R_1$ and $R_2$ are as previously defined); and (3) subjecting Compound 6 thus obtained to hydrogenolysis in the presence of a noble metal catalyst, thereby to give Compound 3. Minocycline can be prepared by reductive dimethylation of Compound 3 using formalin in a hydrogen gas atmosphere in the presence of a noble metal catalyst (Japanese Published Examined Patent Application No. 8380/1967, U.S. Pat. No. 3,226,436). It is also known that minocycline can be directly prepared with Compound 6 without isolating Compound 3 by reaction with formalin in a hydrogen gas atmosphere in the presence of a noble metal catalyst (Belgian Pat. No. 696,488).

Use of a dithionite as a reducing agent in the synthesis of tetracycline and derivatives thereof is known in the preparation of 7-chloro-6-demethyl-6-deoxytetracycline from 6-demethyl-6-deoxy-7,11a-dichlorotetracycline (U.S. Pat. No. 3,043,875).

However, the only method used for the step of preparing Compound 3 from Compound 6 is hydrogenolysis in the presence of a noble metal catalyst, and no process using an inexpensive reducing agent has been known so far.

Method 4 mentioned above requires the use of an expensive noble metal catalyst. Furthermore, the properties of Compound 6 offer various problems. This compound, which separates out from the reaction mixture as fine powder after acidification, is very difficult to collect by filtration, and tends to undergo decomposition and epimerization of the dimethylamino group at 4-position during this operation. Compound 6 is sparingly soluble under the acidic conditions adopted in the reaction steps for preparing Compound 3 or minocycline from Compound 6, which requires a large quantity of solvent and results in low productivity. The reaction is time-consuming, and an expensive noble metal catalyst must be used in a large amount in order to accelerate the reaction.

Thus, there has been a demand for simpler reaction steps without using any noble metal catalyst. Under the circumstances, we have continued intensive studies to develop a new process for the manufacture of 7-amino-6-demethyl-6-deoxytetracycline and accomplished this invention.

SUMMARY OF THE INVENTION

According to the process of this invention, Compound 3 can be obtained by reduction of a compound represented by the general formula (I) (hereinafter referred to as Compound 1) using a dithionite as reducing agent.

This invention also provides a method to produce Compound 3 from Compound 2 in one pot.

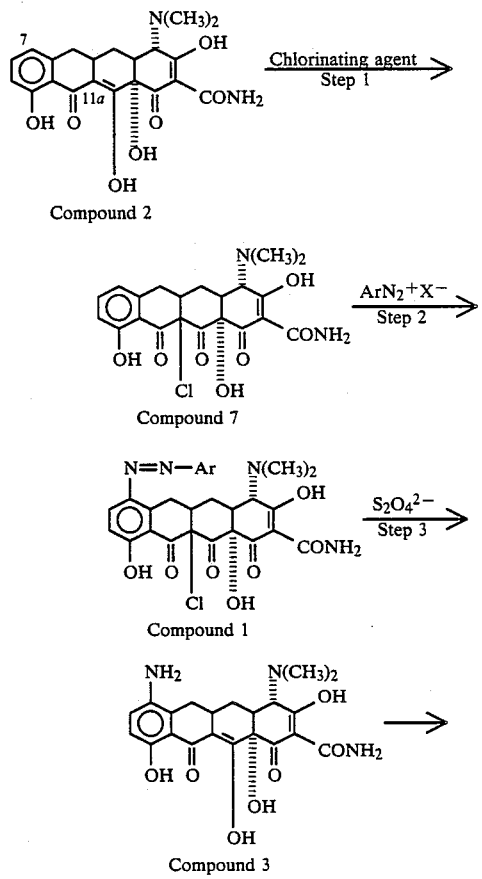

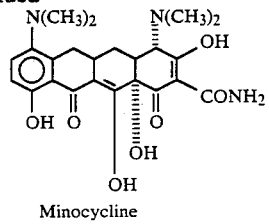

Minocycline (wherein Ar denotes a substituted aryl group, and X stands for the residue of a mineral acid from which hydrogen atom has been eliminated).

DETAILED DESCRIPTION OF THE INVENTION

As the aryl group in Ar, aryl group having 6 to 12 carbon atoms such as phenyl and naphthyl may be used, and the substituted aryl group means the residue of a substituted aromatic primary amine that can be diazotized.

As the substituent group, an electron-attractive group such as nitro, sulfo, cyano and halogen (e.g., Cl and Br) may preferably used. The above-mentioned mineral acid includes hydrochloric acid and sulfuric acid.

Each of the reaction steps is detailed below.

Step 1

Compound 7 can be obtained by chlorinating Compound 2 with a chlorinating agent in a suitable solvent at a temperature in the range of 0° to 50° C., preferably from 10° to 25° C.

Any chlorinating agent capable of generating chlorine cations may be used in this reaction. Illustrative examples include chlorine gas, N-chloro derivatives of lower fatty acid amides (e.g., N-chloroacetamide), N-chloro derivatives of dicarboxylic acid imides (e.g., N-chlorosuccinimide), and lower alkyl esters of hypochlorous acid (e.g., butyl hypochlorite). Particularly, N-chlorosuccinimide is the most preferred.

These chlorinating agents, if used in an equimolar amount based on Compound 2, suffice to complete the reaction. The amount may increase up to 3 to 10 molar equivalents to accelerate the reaction, but the amount in the range of 1.05 to 1.5 molar equivalents is preferable.

As the solvent, water, buffer solutions, lower alcohols (e.g., methanol and ethanol), dimethylformamide and the like may be used either alone or in combination, but the use of water is preferable in order for this step to be followed by the succeeding step on a continuous basis.

The reaction is complete within 24 hours. It takes only 15 to 60 minutes when N-chlorosuccinimide is used in the water.

Step 2

Compound 1 can be obtained by allowing Compound 7 to react with a diazo coupling agent at a temperature in the range of $-10°$ to 30° C., preferably 0°–10° C., in the solvent used in Step 1.

As the diazo coupling agent, diazonium compounds derived from aromatic primary amines that can be diazotized may be used, and those derived from aniline derivatives having one or two electron-attracting substituent groups (e.g., sulfonic acid, nitro, cyano and halogen) at ortho- and/or para-position are preferably used. The diazo coupling agent may be used after being isolated as a stable salt, or used as such in the form of the diazonium solution prepared, which may be concentrated, if required. The diazo coupling agent may be used in an equimolar amount based on Compound 7, but it is usually employed in a larger amount. It is added while monitoring the progress of reaction until compound 7 is no longer detected, and its use in excessive amounts should be avoided. The preferable amount is in the range of 2 to 5 molar equivalents.

Prior to this diazo coupling reaction, the reaction mixture obtained in Step 1 may be concentrated, or may be diluted with water, a buffer solution, a lower alcohol (e.g., methanol and ethanol) or dimethylformamide.

pH of the reaction mixture lowers as the reaction proceeds. It is preferable that the pH level be maintained in the range of 6 to 9, most preferably from 7 to 8, during the whole course of reaction, by addition of an alkali solution or a buffer solution. The reaction is complete in 1 to 4 hours.

Step 3

Compound 3 can be obtained by reducing compound 1 with a dithionite in the solvent used in Step 1 at a temperature in the range of 0° to 60° C., preferably from 0° to 20° C.

The most preferred dithionite is sodium dithionite, which is used in an amount of 3 molar equivalents, based on Compound 1, or more, preferably in the range of 3 to 50 molar equivalents.

pH of the reaction mixture lowers as the reaction proceeds. It is preferable that the pH level be maintained in the range of 5 to 10, most preferably from 7 to 8, during the whole course of reaction, by addition of an alkali solution or a buffer solution. The reaction is complete in 5 minutes to 6 hours.

Compound 1 may be used in the form of the reaction mixture obtained in Step 2. Alternatively, compound 1 is isolated as a precipitate formed by lowering pH of the reaction mixture, and the precipitate may be used.

Further, the reaction for preparing compound 3 from Compound 2 can be carried out without an isolation step in the same one pot. As the solvent to be used in the reactions, water is preferably used.

In each of the reaction steps described above, the desired compound can be isolated and purified, from a concentrate of the reaction mixture as free base or a salt thereof by crystallization, column chromatography, extraction with a solvent, etc.

The following examples and reference examples further illustrate the invention.

EXAMPLE 1

Synthesis of 7-amino-6-demethyl-6-deoxytetracycline from 11a-chloro-6-demethyl-6-deoxy-7-(p-sulfophenylazo)-tetracycline Step 3

At first, 145 mg of 11a-chloro-6-demethyl-6-deoxy-7-(p-sulfophenylazo)tetracycline, obtained in Reference Example 1 described later, was dissolved in 4 ml of water, and the solution was adjusted to pH 7.5 by adding 0.5N aqueous sodium carbonate solution. Then, 399 mg of sodium dithionite was added, and the mixture was stirred at 25° C. for 30 minutes while maintaining the pH in the range of 7 to 8. The resulting reaction mixture was analyzed by high-performance liquid chromatography [JASCO Trirotar Type-II; detector: JASCO Type Uvidec-100 Type III; column: YMC AM-312 (6.0Ø×150 mm, ODS 5 μm); eluent: 0.1M citric acid-acetonitrile (8:2, v/v)+0.1% (wt/wt) sodium pentanesulfonate; 1 ml/min.; detection: UV 254 nm; retention time: 4.51 minutes] (hereinafter referred to as HPLC, and the same shall be applied hereinafter). It was recognized that 81 mg (yield: 82%) of 7-amino-6-demethyl-6-deoxytetracycline had been formed. The reaction mixture was passed through a column packed with Mitsubishi Diaion HP-20 (product of Mitsubishi Kasei Corporation) and the column was washed with water. The adsorbed portion was eluted with water-methanol (3:7, v/v), and the eluate was concentrated in vacuo. The concentrate was freeze-dried, to give 45 mg (yield: 46%) of Compound 3 as pale yellow powders. This compound was idential with the authentic sample separately prepared by the method described in J. Med. Chem., 10, 44 (1967), when comparing their physicochemical properties (HPLC, UV and MS data) with each other.

EXAMPLE 2

Synthesis of 7-amino-6-demethyl-6-deoxytetracycline from 6-demethyl-6-deoxytetracycline by one-pot reaction p-Sulfophenyldiazonium chloride was prepared in the same manner as Reference Example 1.

To a suspension of 1.0 g of 6-demethyl-6-deoxytetracycline in 60 ml of water, were added 2.4 ml of 1N-HCl and 338 mg of N-chlorosuccinimide, and the mixture was stirred at 25° C. for 30 minutes (preparation of 11a-chloro-6-demethyl-6-deoxy-tetracycline; Step 1). The reaction mixture was cooled to 0° to 5° C., and 1N-NaOH solution was dropwise added to adjust pH to 7.5 thereby, while maintaining the temperature in that range. Then, 26 ml of p-sulfophenyldiazonium chloride solution prepared above was then dropwise added at that temperature while maintaining the pH in the range of 7.5 to 8.0 by dropwise addition of 0.5N-Na$_2$CO$_3$ solution [preparation of 11a-chloro-6-demethyl-6-deoxy-7-(p-sulfophenylazo)tetracycline; Step 2]. The pH of the reaction mixture was adjusted to 8.0 by addition of 0.5N-Na$_2$CO$_3$ solution, and 4.2 g of sodium dithionite was added. The resulting mixture was stirred at 25° C. for 1 hour while maintaining the pH in the range of 7.5 to 8.0 by addition of 0.5N-Na$_2$CO$_3$ solution. Analysis by HPLC in the same manner as Example 1 showed that 597 mg of 7-amino-6-demethyl-6-deoxytetracycline was prepared (yield: 57% based on 6-demethyl-6-deoxytetracycline). The reaction mixture was subjected to the same purification procedure in Example 1, to give 418 mg of 7-amino-6-demethyl-6-deoxytetracycline (yield: 40% based on 6-demethyl-6-deoxytetracycline) (Step 3).

EXAMPLE 3

Synthesis of 7-amino-6-demethyl-6-deoxytetracycline from 6-demethyl-6-deoxytetracycline via 11a-chloro-6-demethyl-6-deoxy-7-(p-nitrophenylazo)-tetracycline To a suspension of 300 mg of 6-demethyl-6-deoxytetracycline in 20 ml of water, were added 0.7 ml of 1N-HCl and 101 mg of N-chlorosuccinimide, and the mixture was subjected to reaction in the same manner as Reference Example 1, to give 11a-chloro-6-demethyl-6-deoxytetracycline (Step 1).

To this reaction mixture, was added 259 mg of p-nitrophenyldiazonium pentafluorophosphate while maintaining the temperature in the range of 0° to 5° C. and the pH in the range of 7.5 to 8.0, and the mixture was stirred under the same conditions for 2 hours. The mixture was adjusted to pH 2 by addition of concentrated hydrochloric acid to separate out a precipitate. The precipitate was collected by centrifugation, and the solid thus obtained was dried under reduced pressure, to obtain 396 mg of 11a-chloro-6-demethyl-6-deoxy-7-(p-nitrophenylazo)tetracycline as a crude product (yield: 86%) (Step 2).

Then, 120 mg of the crude product was suspended in 4 ml of water, and the suspension was adjusted to pH 8.0 by addition of 0.5N-$Na_2CO_3$ solution. Further, 525 mg of sodium dithionite was added, and the mixture was stirred at 25° C. for 4 hours while maintaining the pH in the range of 7.5 to 8.0. The resulting mixture was treated in the same manner as Example 1, to obtain 56 mg of 7-amino-6-demethyl-6-deoxytetracycline (yield: 61% based on 6-demethyl-6-deoxytetracycline) (Step 3).

REFERENCE EXAMPLE 1

Synthesis of 11a-chloro-6-demethyl-6-deoxy-7-(p-sulfophenylazo)-tetracycline (Steps 1 and 2 being carried out in one pot)

At first, 2.0 g of 6-demethyl-6-deoxytetracycline was dissolved in a mixture of 6.0 ml of water and 4.8 ml of aqueous 1N-HCl solution, 0.68 g of N-chlorosuccinimide was added to the solution, and the resulting mixture was stirred at 25° C. for 15 minutes. Analysis by HPLC showed that the reaction had proceeded quantitatively (Step 1).

A solution of 0.78 g of sodium carbonate and 2.55 g of sulfanilic acid in 55 ml of water was cooled to 0° C., and 6 ml of an aqueous solution containing 1.11 g of sodium nitrite was added. Further, 15 ml of cold 2N-HCl was added while maintaining the temperature in the range of 0° to 5° C., to form p-sulfophenyldiazonium chloride. Starch iodide paper was used in recognizing the end of reaction.

The reaction mixture obtained in Step 1 was cooled to 0° to 5° C., and the pH was adjusted to 7.5 by dropwise addition of aqueous 1N-NaOH solution while keeping the temperature there. The solution of p-sulfophenyldiazonium chloride prepared above was entirely added dropwise. During the whole course of reaction, the temperature was held in the range of 0° to 5° C. and pH was maintained in the range of 7.5 to 8.0 by dropwise addition of aqueous 0.5N $Na_2CO_3$ solution. Stirring was continued for an additional 2.5 hours under the same conditions, and the reaction mixture was adjusted to pH 2.5 by addition of concentrated hydrochloric acid. A precipitate which separated out was collected by centrifugation and dried under reduced pressure, to give 2.89 g (yield: 89%) of 11a-chloro-6-demethyl-6-deoxy-7-(p-sulfophenylazo)tetracycline (Step 2).

REFERENCE EXAMPLE 2

Synthesis of minocycline(6-demethyl-6-deoxy-7-dimethylaminotetracycline) from 7-amino-6-demethyl-6-deoxytetracycline To a solution of 12.8 mg of 7-amino-6-demethyl-6-deoxytetracycline in 2.4 ml of methanol, were added 0.5 ml of 1N-HCl, 0.1 ml of 37% formalin and 5 mg of 10% palladium-carbon, and reductive dimethylation was carried out at 25° C., for 3.5 hours in a hydrogen gas atmosphere under atmospheric pressure. Analysis of the reaction mixture by HPLC showed that 16.3 mg (quantitative yield) of minocycline dihydrochloride monohydrate (retention time: 5.16 minutes) was formed.

What is claimed is:

1. A process for producing 7-amino-6-demethyl-6-deoxytetracycline which comprises reducing a 11a-chloro-6-demethyl-6-deoxy-7-(substituted arylazo)tetracycline represented by the following general formula (I),

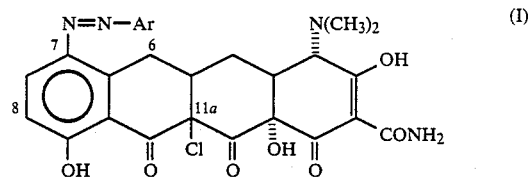

(wherein Ar is a substituted aryl group), using a dithionite as the reducing agent.

2. The process according to claim 1, wherein Ar is a phenyl group having one or two electron-attracting substituent groups at ortho- and/or para-position.

3. The process according to claim 1, wherein Ar is a member selected from the group consisting of p-nitrophenyl, p-sulfophenyl and p-(substituted sulfonyl)-phenyl groups.

4. The process according to claim 1, wherein said dithionite is sodium dithionite.

5. The process according to claim 1, wherein the 11a-chloro-6-demethyl-6-deoxy-7-(substituted arylazo)tetracycline has been prepared by chlorinating 6-demethyl-6-deoxytetracycline at 11a-position, followed by reaction with a substituted aryldiazonium salt represented by the formula, $ArN_2^+X^-$ (wherein Ar is as previously defined, and X is the residue of a mineral acid from which hydrogen atom has been eliminated).

6. The process according to claim 5, wherein the 11a-chloro-6-demethyl-6-deoxy-7-(substituted arylazo)tetracycline is submitted to subsequent reduction without being isolated from the reaction mixture.

7. The process according to claim 5, wherein the final product is synthesized from 6-demethyl-6-deoxytetracycline in one pot.

* * * * *

UNITED STATES PATENT AND TRADEMARK OFFICE
CERTIFICATE OF CORRECTION

PATENT NO. : 4,849,136
DATED : July 18, 1989
INVENTOR(S) : YUTAKA SAITO, ET AL.

It is certified that error appears in the above-identified patent and that said Letters Patent is hereby corrected as shown below:

IN [57] ABSTRACT

That portion of the structure for Compound 2 reading " 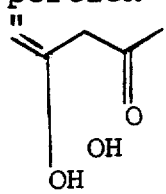 " should read -- 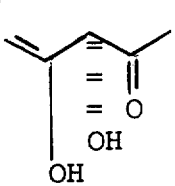 --

IN [56] REFERENCES CITED

Under "U.S. PATENT DOCUMENTS" add:
--3,862,225   1/1975   Conover et al. ..........260/501.17
  4,489,206  12/1984   Cava et al.--. ..........260/351.5

COLUMN 8

Line 20, "reduding" should read --reducing--.

Signed and Sealed this

Twenty-second Day of May, 1990

Attest:

HARRY F. MANBECK, JR.

Attesting Officer          Commissioner of Patents and Trademarks